United States Patent [19]
VanBeek et al.

[11] Patent Number: 5,211,644
[45] Date of Patent: May 18, 1993

[54] PROCESS AND APPARATUS FOR A DERMAL GRAFT

[75] Inventors: Allen L. VanBeek, Edina; Alfred A. Iversen, Minnetonka Beach, both of Minn.

[73] Assignee: PMT Corporation, Chanhassen, Minn.

[21] Appl. No.: 763,281

[22] Filed: Sep. 20, 1991

[51] Int. Cl.$^5$ ............................................ A61M 31/00
[52] U.S. Cl. ........................................ 606/1; 604/51; 604/264; 606/229
[58] Field of Search .............. 606/1, 185, 191, 192, 606/198, 230, 229; 604/51, 164, 264, 93, 96

[56] References Cited

U.S. PATENT DOCUMENTS

| | | | |
|---|---|---|---|
| 3,558,262 | 1/1971 | Duffy et al. | 606/229 X |
| 3,918,455 | 11/1975 | Coplan | 606/229 X |
| 4,453,928 | 6/1984 | Steiger | 604/264 X |
| 4,660,546 | 4/1987 | Herrick et al. | 604/264 X |
| 4,721,506 | 1/1988 | Teves | 604/51 |
| 4,813,929 | 3/1989 | Semrad | 604/51 |
| 4,862,891 | 9/1989 | Smith | 606/191 |
| 4,940,458 | 7/1990 | Cohn | 604/51 |
| 5,053,046 | 10/1991 | Janese | 604/51 X |
| 5,071,410 | 12/1991 | Pazell | 604/164 |

OTHER PUBLICATIONS

Desilets-Hoffmann Catheter Introducer, Radiology, vol. 85, Jul.-1965, pp. 147-148.

Primary Examiner—Peter A. Aschenbrenner
Attorney, Agent, or Firm—Gerald E. Helget

[57] ABSTRACT

The process and apparatus for an autologous dermal graft transfer provides for the easy and accurate placement of dermal grafts during plastic surgery, typically for the filling of wrinkles or scars.

2 Claims, 12 Drawing Sheets

PROCESS AND APPARATUS FOR A DERMAL GRAFT

BACKGROUND OF THE INVENTION

1. Field of the Invention

The present invention is for surgical instruments, and more particularly, pertains to a process and apparatus for an autologous dermal graft transfer including, dermal dilators and dermal guides for plastic surgery, reconstructive surgery or collagen.

2. Description of the Prior Art

No instruments have been specifically developed for dermal graft procedures. Simple spinal needles have been used to place dermal grafts.

This is a new concept regarding the treatment of wrinkles because prior art bovine collagen introduces a foreign protein. In some instances, this foreign protein may cause an antigenic reaction or a delayed cellular immune reaction. There is some concern whether injectable bovine collagen is associated with a disease called adjuvant disease.

The present invention overcomes the disadvantages of the prior art by replacing the use of bovine collagen injections. It would replace the direct surgical excision of some wrinkle lines and would replace silicone injections into the dermis which have been used in remote history. Bovine collagen results do not last long. The present invention will also replace the compound called Fibril as a substance for treating wrinkles.

SUMMARY OF THE INVENTION

The general purpose of the present invention is a dermal graft system which improves on basic spinal needle insertion techniques by allowing more accurate and easy placement of the graft in a remote location under the skin.

According to one embodiment of the present invention, there is provided a process and apparatus for a dermal graft. In using this device, the dermis material used is autologous dermis, which means the dermis is from the person himself. Autologous dermal grafts are very similar to skin grafting for burns. Therefore, there is no problem with graft rejection. This autologous tissue is obtained from tissue that is being disposed of because it has been removed in conjunction with another operation, such as a blepharoplasty, which is the removal of extra wrinkly skin from the eyes, or face lift, which is removal of extra skin from the area of the face. Dermal grafts may also be harvested from other regions should no dermis be available. Instead of disposing of this tissue, one then, by processing the tissue surgically and removing the epithelium, are able to use the person's own dermal collagen from the skin to correct the wrinkles. In other words in essence what one is doing, instead of using foreign collagen harvested from animals, one is using the person's own collagen and placing it in a wrinkle to treat the wrinkle. Dermal grafting is well accepted in surgery, and has been preformed for over three decades. However, this process of taking a small amount of autologous collagen and exactly positioning it in a strategic area with the apparatus, is a new procedure, and has the advantage of not introducing foreign protein into the person. In experience, this is a more permanent replacement for the treatment of wrinkles. The effects of collagen and Fibril, for instance, may only last for 6 to 12 months, ore even less time, and then need to be redone. In this process, there is evidence that for periods of three years (or more), this material stays in a permanent way. Unlike autologous fat which has been utilized, this is autologous dermis, and in experience, stays on a permanent basis. Autologous fatty tissue is absorbed by the body.

The apparatus can also be used for the introduction of dermis, cartilage and other autologous materials for the treatment of contoured deformities or loss of tissue or atrophy of tissue following trauma. Specifically for depressed scars. The apparatus can also be utilized for the precise placement of cartilage in the reconstruction of the nose or lip, and potentially in areas of the cheek or facial skin, in an area which there is a concavity that has followed trauma or disease.

The apparatus can be used in reconstruction of curvatures of the ears where cartilage is being placed. Also, this device can be utilized for the transferring of small bony fragments, if necessary, for bone grafts in strategic areas where on wants to avoid scars. The advantage of the apparatus is that one can place tissue at a remote site in an exact way without causing visible scarring. The scars will be associated with the needle puncture, but those scars are usually put in a hidden area, such as the scalp, behind the ear, inside the mouth, or in other areas where the scarring is concealed. The process is primarily going to be used in reconstructive and plastic surgery where the cosmetic result is important to the individual having the procedure done.

The material which is to be transferred using this process is usually harvested or taken from portions of tissue which are going to be disposed of or thrown because they have been removed intentionally with a face lift or they have been removed because of an unsightly scar, or they have been harvested intentionally. For instance, the rib is a common site for removing extra cartilage. The ear is a common site for removing autologous cartilage, in scars, in face lifts, eyelid surgery, and abdominal plastys are common areas where donor material is taken from.

One key of the present invention the exact placement of the dermal graft for surgical treatment for wrinkles or scars.

Significant aspects and features of the present invention include a process and apparatus for a dermal graft for the surgical treatment of an individual with their own dermis.

Having thus described embodiments of the present invention, it is a principal object hereof to provide a process and apparatus for a dermal graft.

One object of the present invention is that the dermal graft is from individuals, such as from a face lift, scar revision or from a plepharoplasty. Dermis can also be selected from other areas of the individual's body.

Another object of the present invention are potential areas for use of this technique including glabbellar graft, nasal cartilage graft or nasal labial fold graft.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

Figure 6:
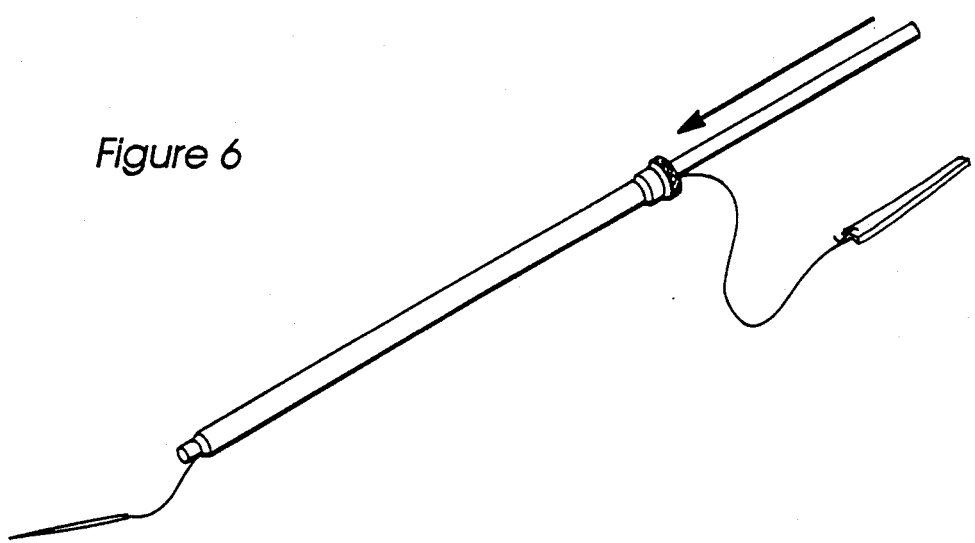
Figure 7:
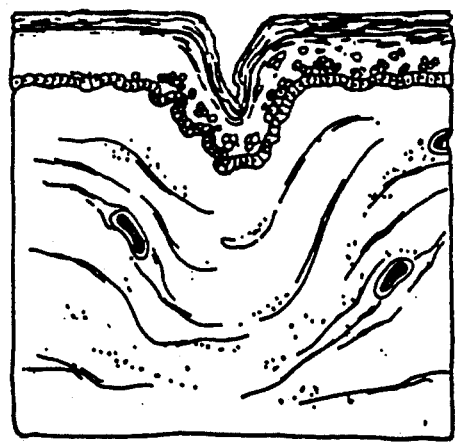
Figure 8:
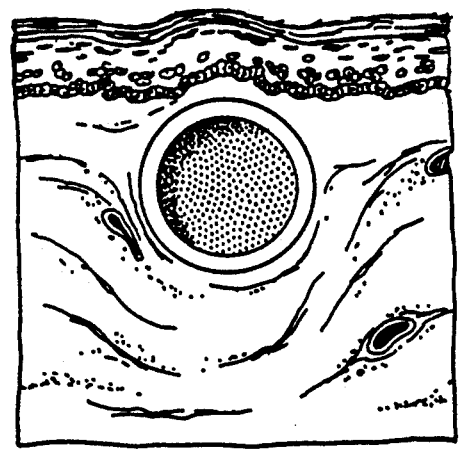
Figure 9:
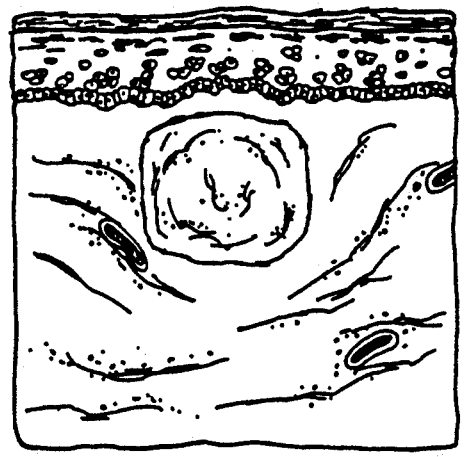
Figure 10:
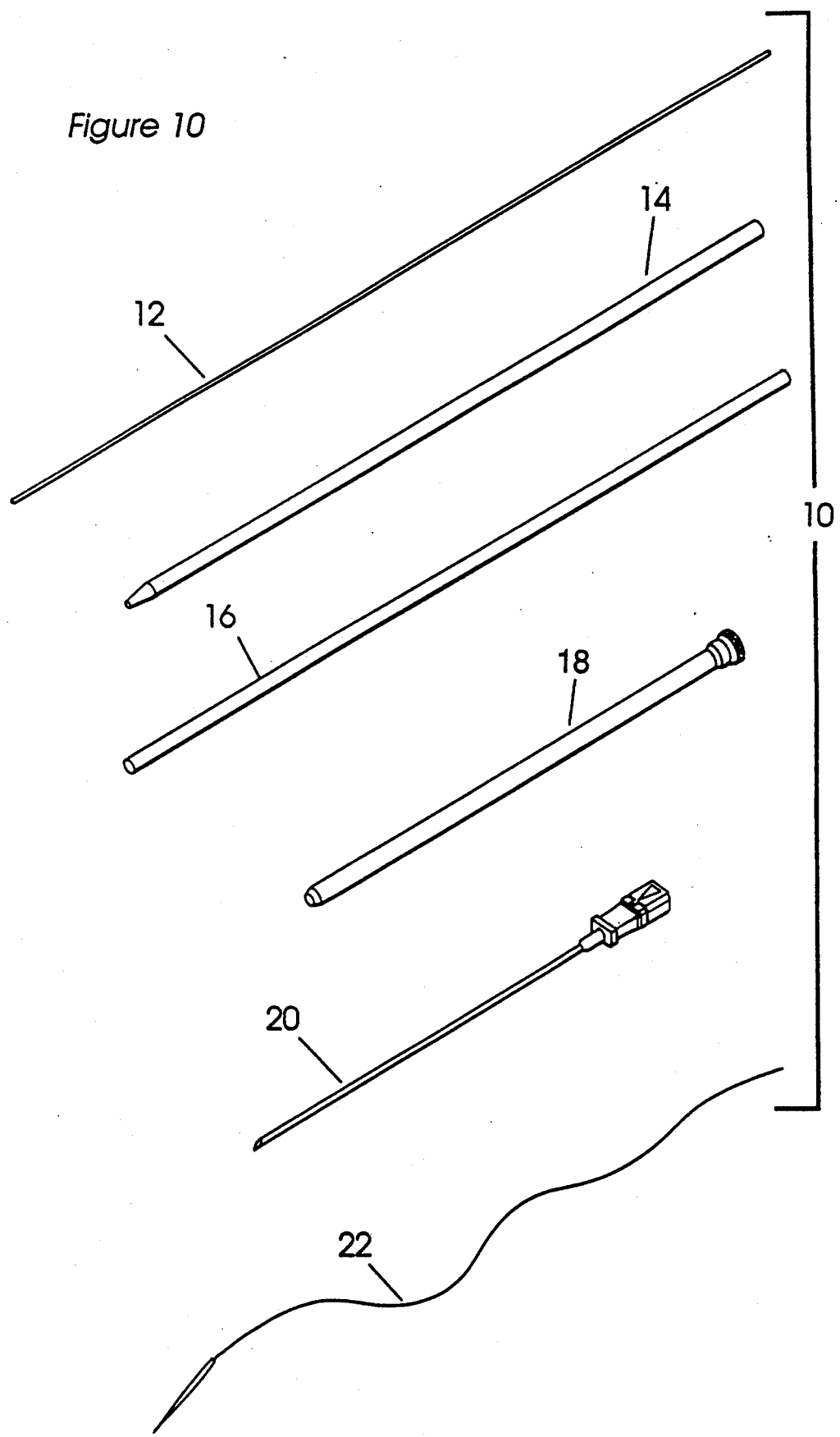
Figure 11A:
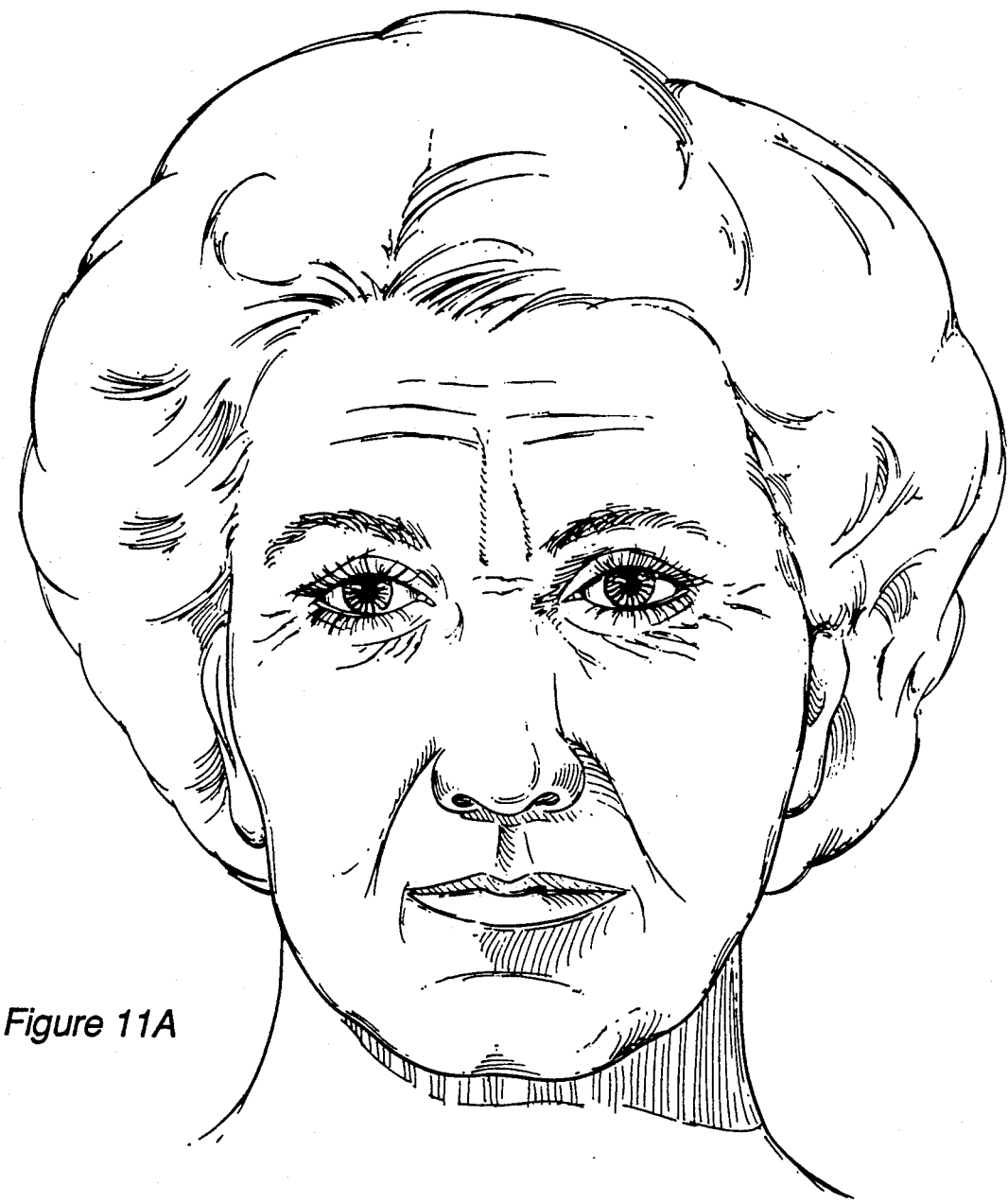
Figure 11B:
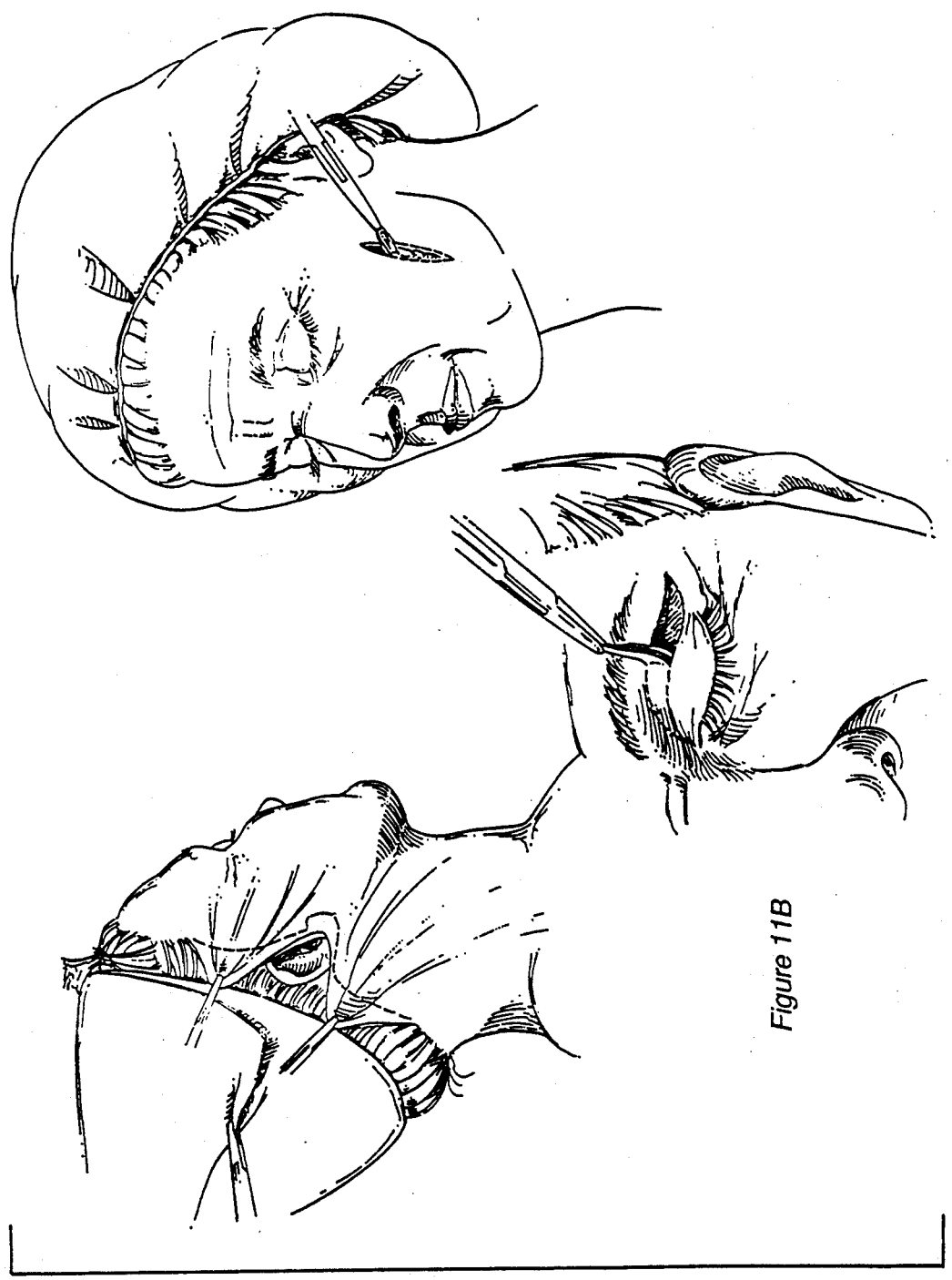
Figure 12A:
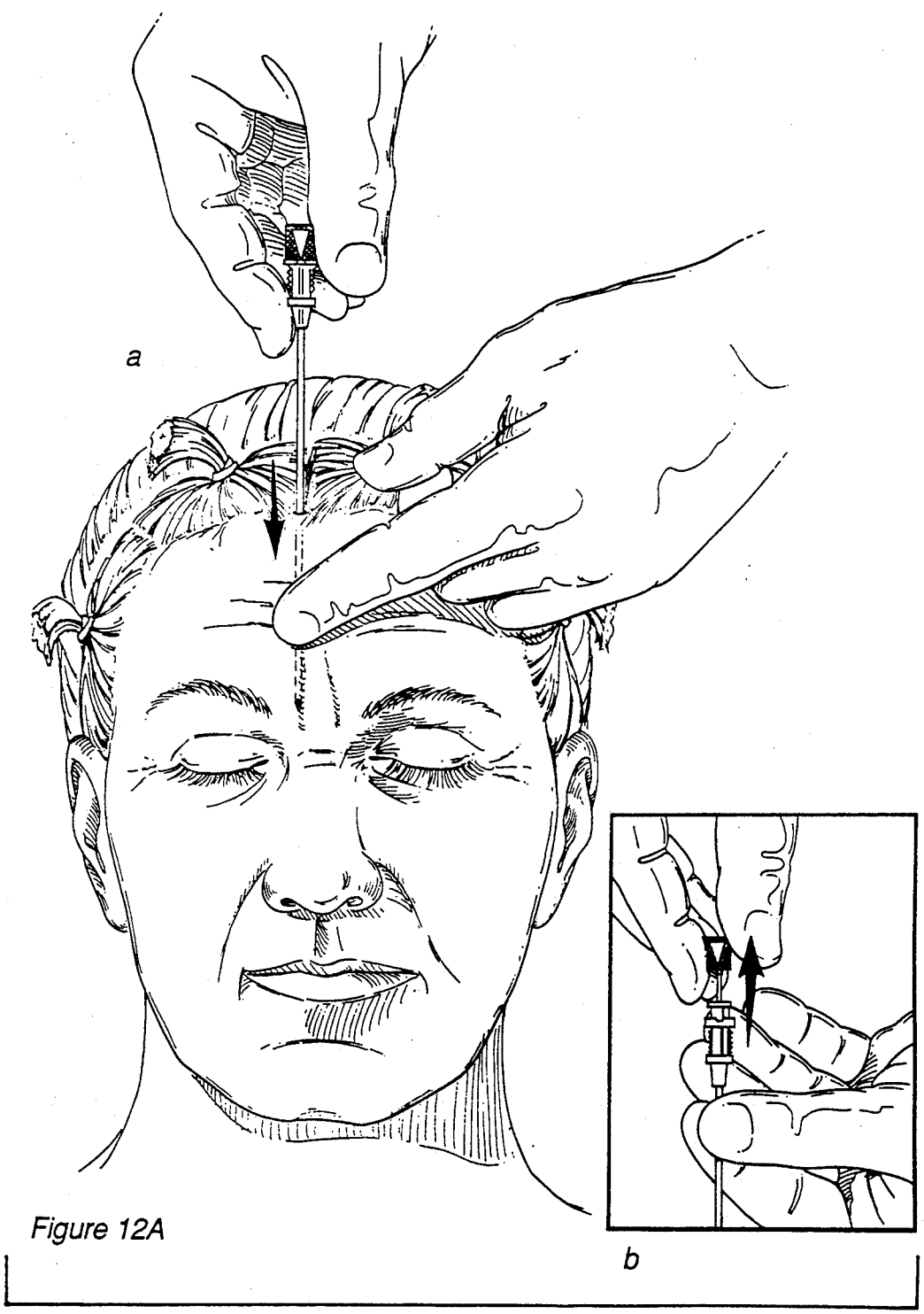
Figure 12B:
Figure 12C:
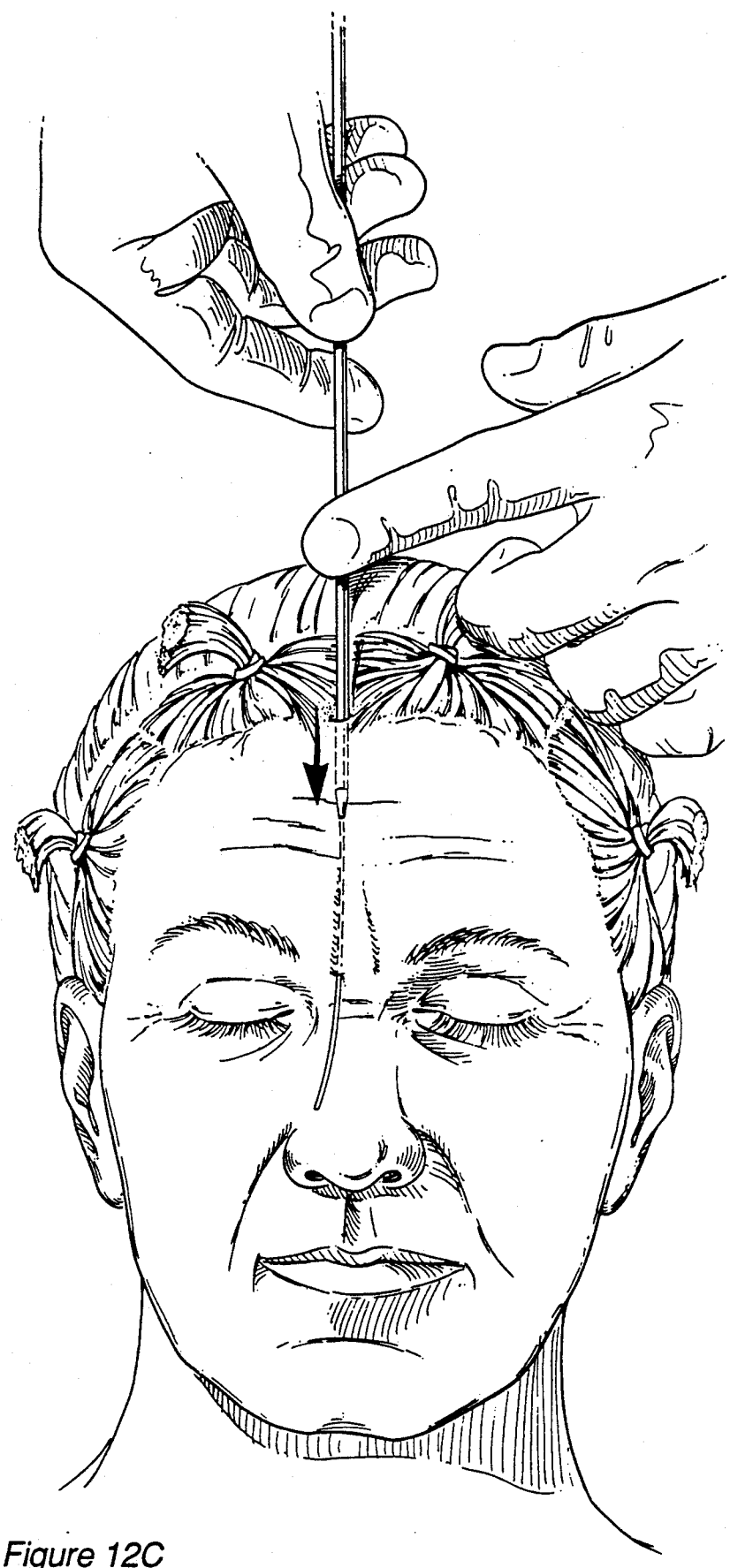
Figure 12D:
Figure 12E:
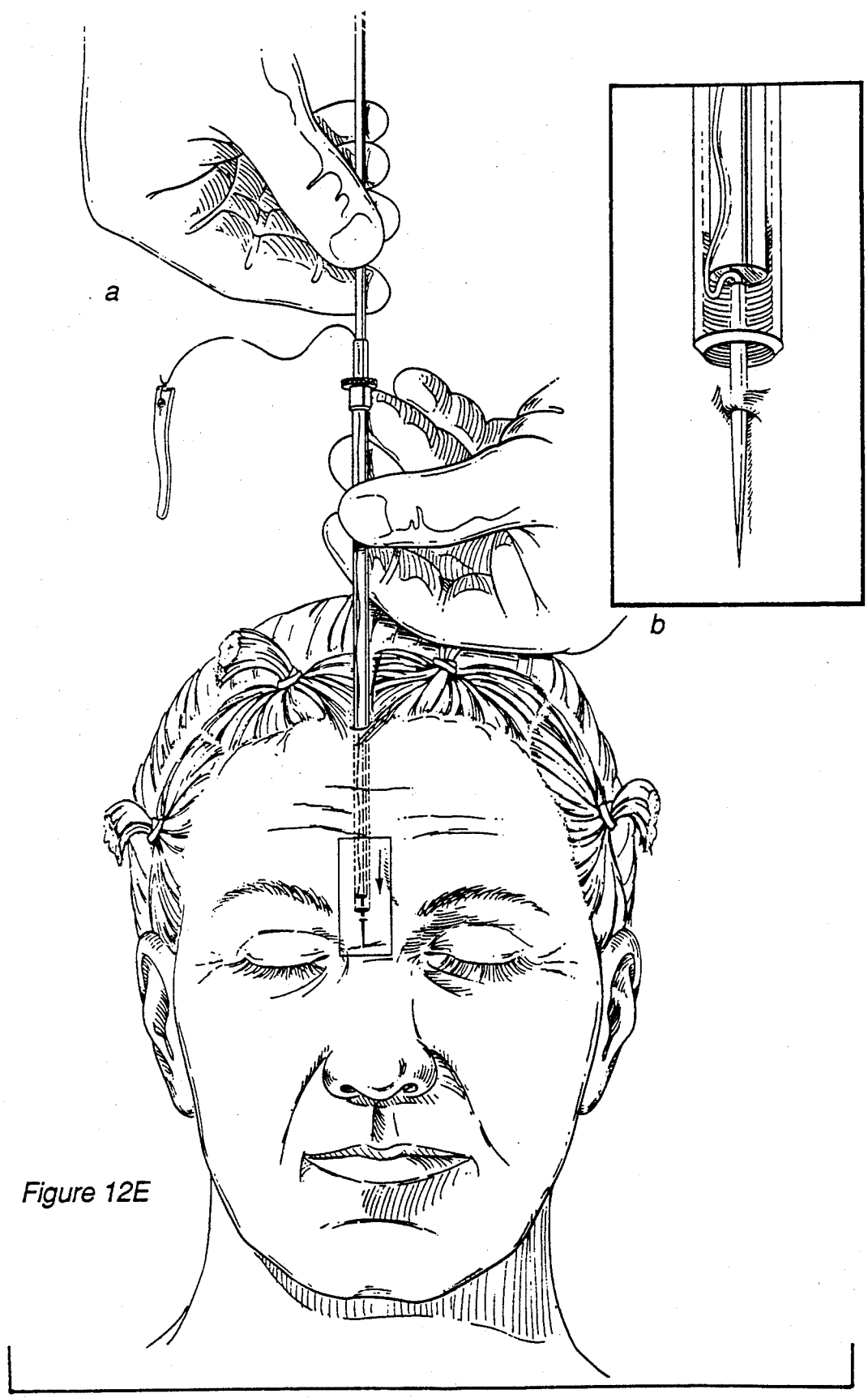
Figure 12F:
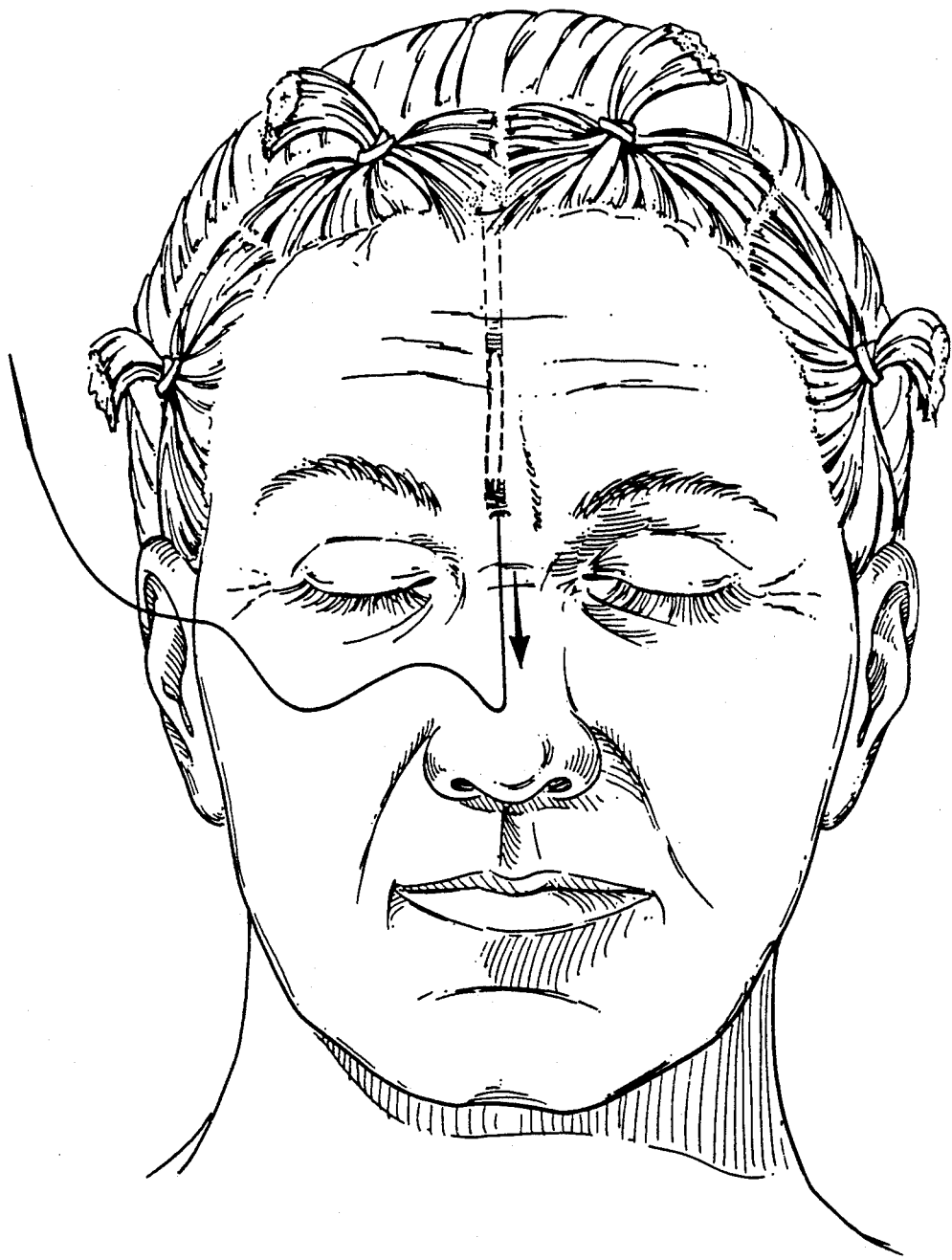

FIG. illustrates step 5 of the process and apparatus for a dermal graft;

FIG. 6 illustrates step 6 of the process and apparatus for a dermal graft;

FIG. 7 illustrates a skin wrinkle;

FIG. 8 illustrates a dermal cannula inserted into the dermis;

FIG. 9 illustrates a dermal skin graft in place in the dermis;

FIG. 10 illustrates an exploded view of the components of the dermal graft system;

FIG. 11A-11B illustrate potential areas for use of the process for dermal graft, and the potential donor sites for dermal graft material; and, FIGS. 12A-12F graphically illustrate the steps of the dermal graft procedure.

DETAILED DESCRIPTION OF THE PREFERRED EMBODIMENTS

A dermal graft system 10 of the present invention includes five components as illustrated in accompanying drawings.

Guidewire—a length of stainless steel wire;
2. Dermal Tunneler—disposable spinal needle;
3. Dermal Dilator—sharp tapered hollow tunneling cannula;
4. Dermal Transfer Cannula—hollow large bore stainless cannula; and,
5. Transfer Obturator—blunt ramrod.

The steps of the process of the present invention are now summarized as follows:

A. The 18 gauge needle by way of example is inserted under the skin to the location at which the dermis is to be placed.

B. The guidewire is then inserted into the needle, and the needle is removed leaving the guidewire in place.

C. The dermal dilator is then slipped over the guidewire widening the path under the skin marked by the guidewire.

D. The dermal transfer cannula is then slid into place over the dermal dilator and the dermal Dilator is removed.

E. The dermal graft is then tied to a suture/needle combination (4.0 or other similar absorbable suture) and is pushed through the dermal transfer cannula with the transfer obturator until the needle punctures the skin at the desired graft site. The needle is then grabbed and pulled away from the site until the dermal graft comes to rest against the skin.

Figure 1:
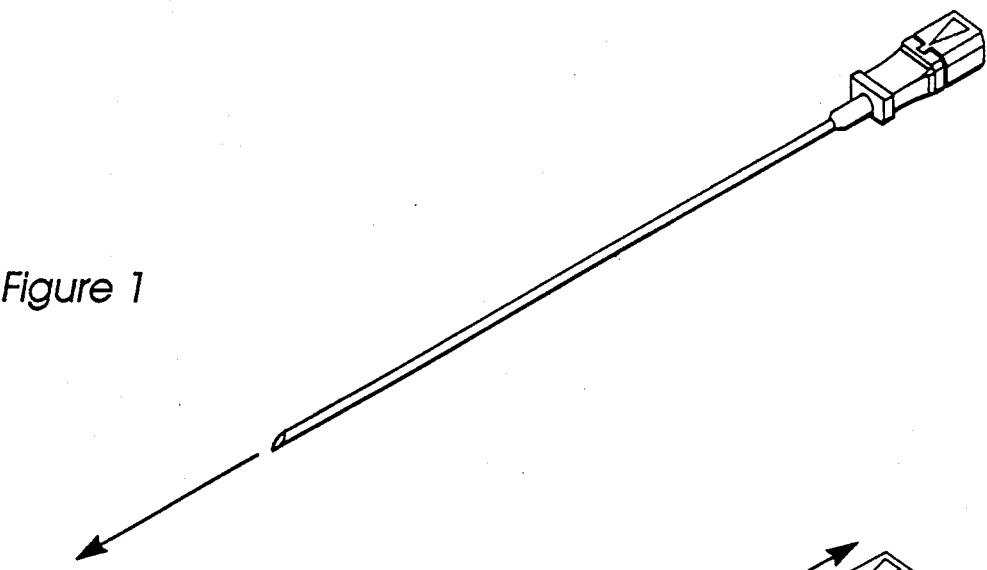
FIG. 1 illustrates step of the process and apparatus for a dermal graft.

The figures are now described in detail:

FIG. 1 illustrates step 1 and it refers to a needle. This is a dermal needle and has a stylet. This dermal needle will be utilized to create the initial channel in the dermis of the skin that is to be treated.

Figure 2:
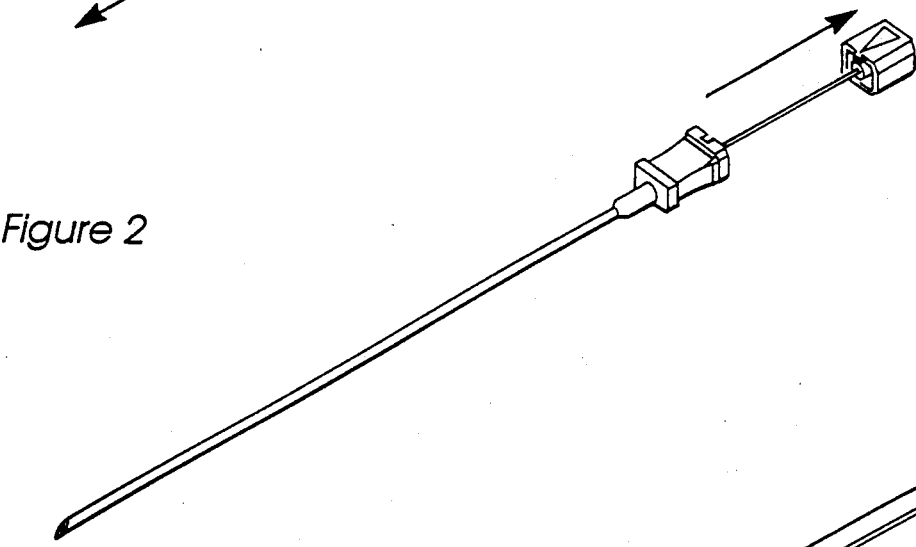
FIG. 2 illustrates step 2 of the process and apparatus for a dermal graft.

FIG. 2 illustrates step 2. After forming the channel, the stylet is then removed.

Figure 3:
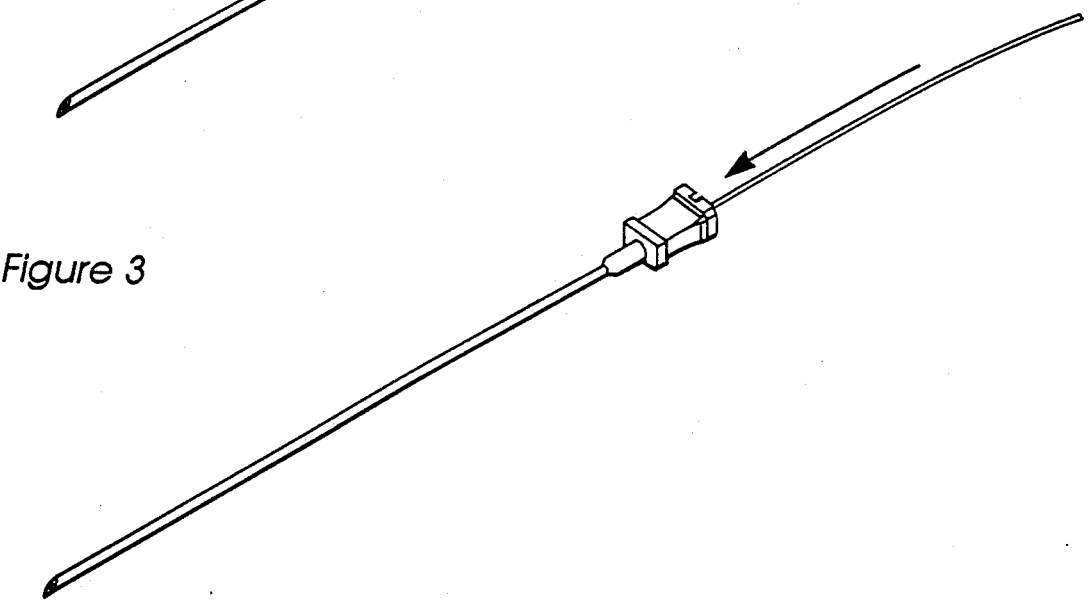
FIG. 3 illustrates step 3 of the process and apparatus for a dermal graft.

FIG. 3 illustrates step 3. The dermal guidewire is introduced through the hub and through the shaft of the needle and brought to the outside of the skin.

Figure 4:
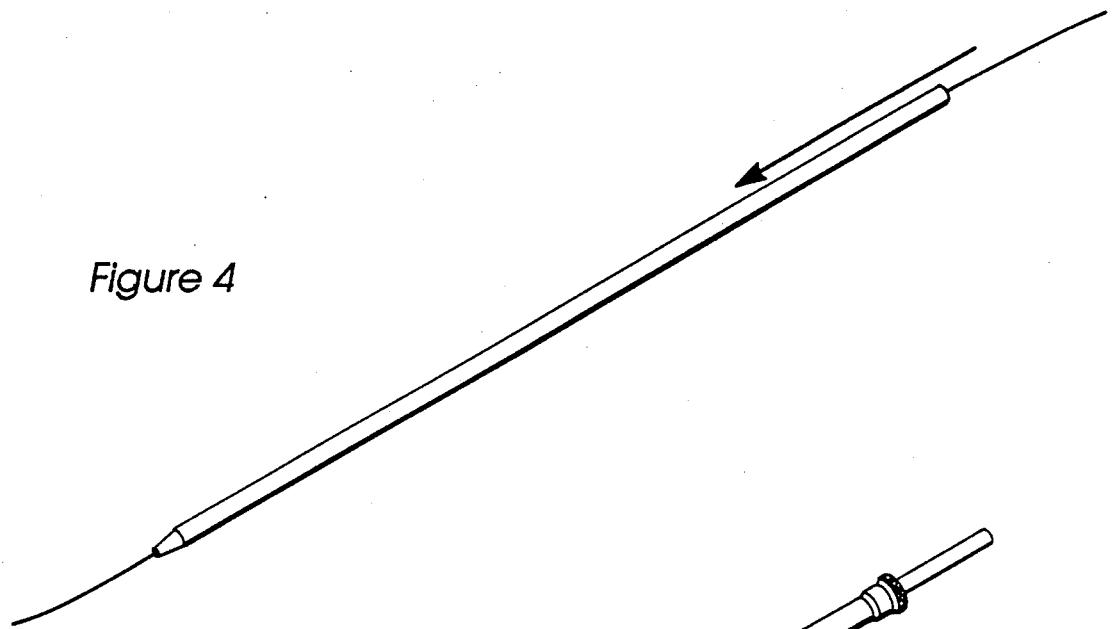
FIG. 4 illustrates step 4 of the process and apparatus for a dermal graft.
Figure 5:
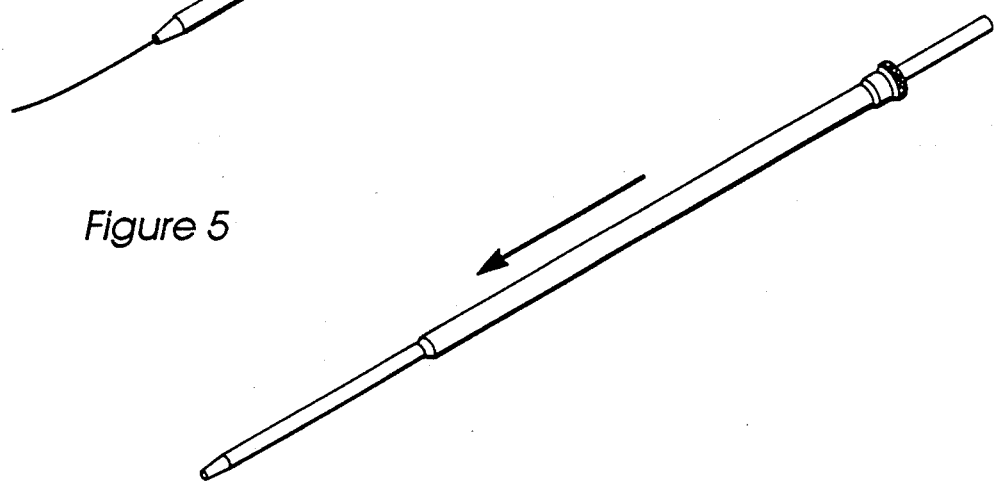

FIG. 4 illustrates step 4. The needle is then removed, leaving the guidewire in position. The dermal dilator is then threaded over top of the guidewire. The dermal dilator has a channel through the middle of it that allows the dilator to be put over top of the guidewire, and therefore, dilate the exact area of the dermis which the surgeon has selected for treatment. Once the dermal dilator is introduced and in position, the guidewire is removed.

FIG. illustrates step 5. The dermal transfer cannula is then placed over top of the dermal dilator and introduced into the channel created in the dermis of the skin. The dermal dilator is then removed, leaving the cannula in the proper position. A portion of dermis, which as been de-epithelized and properly sized by the surgeon will then be attached to the end of an absorbable suture.

FIG. 6 illustrates step 6. The needle on the end of the suture will be introduced into the dermal cannula and be pushed down the shaft of the dermal cannula with a needle pushing device. This needle pushing device will push the needle down the opening in the cannula and eventually push the needle outside the dermal cannula and through the skin. The surgeon will then take the needle and pull the strip of dermis through the dermal transfer cannula to introduce and position the dermal graft in the body. The dermal transfer cannula is removed, and the suture secures the portion of dermis in the appropriate position. The excess suture is trimmed off, perhaps leaving a small portion of suture outside the skin following surgery.

FIG. 7 illustrates a typical skin wrinkle.

FIG. 8 illustrates a dermal cannula inserted into the dermis.

FIG. 9 illustrates a dermal skin graft in place in the dermis.

FIG. 10 illustrates an exploded view of the components of the dermal graft system 10, including in order a guidewire 12, a dermal dilator 14, a obturator 16, a dermal cannula 18, a stylet 20 and a suture assembly 22.

FIGS. 11A-11B illustrate some potential areas for use of the process for dermal graft, and the potential donor sites for dermal graft material.

FIGS. 12A-12F graphically illustrate the steps of the dermal graft procedure

MODE OF OPERATION

The steps of the process and apparatus for a dermal graft in brief are now listed:

1. Insert the dermal needle.
2. Remove stylet.
3. Insert guidewire.
4. Remove needle cannula, place dermal dilator over guidewire, and remove guide wire.
5. Place the dermal transfer cannula over the dermal dilator then remove the dermal dilator.
6. Insert the needle with dermis into the dermal cannula and feed through with the obturator.

The dermal needle is utilized to create the initial channel in the dermis of the skin that is to be treated. After forming the channel, the stylet is then removed and the dermal guidewire is introduced through the hub and through the shaft of the needle and brought to the outside of the skin. This needle is then removed, leaving the guidewire in position. The dermal dilator will then be threaded over top of the guidewire. The dermal dilator has a channel through the middle of it that allows the dilator to be put over top of the guidewire, and therefore, dilate the exact area of the dermis which the surgeon has selected for treatment. Once the dermal dilator is introduced and in position, the guidewire is removed. The dermal cannula is then placed over top of the dilator and introduced into the channel created in the dermis of the skin. The dermal dilator is then removed, leaving the cannula in the proper position. A portion of dermis, which has been de-epithelialized and properly sized by the surgeon will then be attached to the end of an absorbable suture. The needle on the end of the suture will be introduced into the dermal transfer cannula and be pushed down the shaft of the dermal transfer cannula with a needle pushing device. This needle pushing device (obturator) will push the needle down the opening in the cannula and eventually push the needle outside the dermal transfer cannula and through the skin. The surgeon will then take the needle and pull the strip of dermis through the dermal transfer cannula to introduce and position the dermal in the body. The dermal transfer cannula is removed and the suture secures the portion of dermis in the appropriate position. The excess suture is trimmed off, perhaps leaving a small portion of suture outside the skin following surgery.

Various modifications can be made to the present invention without departing from the apparent scope hereof. The instrument can be packed in a sterile bag or on a sterile preformed tray, such as in the order of FIG. 10. Any suitable materials can be molded for the instruments, including polymers or the like, especially one time use and disposal. Other types of harvesting devices could also be utilized.

We claim:

1. Process for performing a dermal graft surgical procedure comprising the steps of:
   a. inserting a dermal needle and removing an obturator;
   b. inserting a guidewire and removing the dermal needle, leaving the guidewire in place;
   c. pacing a dermal dilator over the guidewire and removing the guidewire;
   d. passing a dermal transfer cannula over the dermal dilator, removing the dermal dilator;
   e. inserting a needle with dermal graft material attached thereto;
   f. using the cannula obturator to advance the needle through the dermal cannula until the needle exits the skin;
   g. pulling the dermal graft into final position.

2. Process for performing a dermal graft surgical procedure comprising the steps of:
   a. inserting a dermal needle and removing an obturator;
   b. inserting a guidewire and removing the dermal needle, leaving the guidewire in place;
   c. pacing a dermal dilator over the guidewire and removing the guidewire;
   d. passing a dermal transfer cannula over the dermal dilator, removing the dermal dilator;
   e. inserting a needle with dermal graft material attached thereto;
   f. using the cannula obturator to advance the needle through the dermal cannula until the needle exits the skin;
   g. pulling the dermal graft into position;
   h. removing the cannula; and,
   i. positioning the graft with tension applied through the suture.

* * * * *

UNITED STATES PATENT AND TRADEMARK OFFICE
CERTIFICATE OF CORRECTION

PATENT NO. : 5,211,644
DATED : May 18, 1993
INVENTOR(S) : Allen L. VanBeek and Alfred A. Iversen It is certified that error appears in the above-identified patent and that said Letters Patent is hereby corrected as shown below:

Column 3, line 1, after "step" and before "of", insert --1--.

Column 4, line 13, after "FIG." and before "illustrates", insert --5--.

Signed and Sealed this

Eighteenth Day of January, 1994

Attest:

BRUCE LEHMAN

Attesting Officer *Commissioner of Patents and Trademarks*